United States Patent [19]

Schenk

[11] 4,258,212
[45] Mar. 24, 1981

[54] PROCESS FOR PREPARING POLYSULFIDE CHAIN TERMINATOR

[75] Inventor: William N. Schenk, Peninsula, Ohio

[73] Assignee: The B. F. Goodrich Company, Akron, Ohio

[21] Appl. No.: 104,227

[22] Filed: Dec. 17, 1979

[51] Int. Cl.$^3$ ............................................. C07C 149/00
[52] U.S. Cl. ....................................... 568/22; 528/373
[58] Field of Search .......................................... 260/608

[56] References Cited

U.S. PATENT DOCUMENTS 2,754,333   7/1956   McCarthy ............................ 260/608

OTHER PUBLICATIONS

E. Gasson et al., J. Chem. Soc. (1948) pp. 44–46.
E. Reid, Org. Chem. of Bivalent Sulfur, III, p. 365, Chem. Publ. Co., N.Y. 1960.
G. Bennett, J. Chem. Soc. (1921), 119, 418–425.
Gilman, Org. Chem. I, 2nd Edition, 861–866.

Primary Examiner—Donald G. Daus
Assistant Examiner—M. C. Eakin
Attorney, Agent, or Firm—Alfred D. Lobo; J. Hughes Powell, Jr.

[57] ABSTRACT

A process is disclosed for preparing a mixture of hydroxyl containing di- and trisulfides, from either 2-mercaptoethanol or 3-mercaptopropanol, directly in two steps, without the formation of deleterious byproducts. Precise control of process conditions (a) in a first step in which the disulfide is formed, includes oxidation of mercapto-lower alkanol with a stoichiometric amount of $H_2O_2$ while maintaining the pH and temperature of a relatively dilute aqueous reaction mixture within a specific narrow range; and, (b) in a second step in which a predetermined portion of the disulfide is converted substantially exclusively to the trisulfide, requires controlled heating of the reaction mixture to a temperature not to exceed 100° C. The process may be carried out in a single reaction vessel, and directly yields a preselected distribution of disulfide and trisulfide in the mixture. The mixture is especially useful as a chain terminator in the preparation of hydroxyl-terminated liquid polymers having an aliphatic polymeric backbone and sulfide linkages near the terminal portions of the polymer molecule (referred to as "HTPS" polymers).

6 Claims, No Drawings

PROCESS FOR PREPARING POLYSULFIDE CHAIN TERMINATOR

BACKGROUND OF THE INVENTION

The commercial preparation of hydroxyl-terminated liquid polymers having an aliphatic polymeric backbone and sulfide likages near the terminal portions of the polymer molecule has increased steadily over the past few years. The successful preparation of these liquid polymers (hereinafter referred to as "HTPS polymers" for brevity), depends upon the selection of chain terminator, and the amount of chain terminator used.

The preparation of HTPS polymers is described in U.S. Pat. Nos. 3,910,992; 4,013,710; and 4,120,766 ("the '766 patent"); the disclosures of each of which is incorporated by reference herein as if fully set forth. In particular, the '766 patent discloses the reaction of at least one vinylidene monomer with at least one hydroxyl-containing disulfide, which reaction provides particularly desirable HTPS polymers believed to have the formula

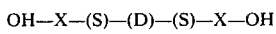

wherein, X is $(CH_2O)_m(CH_2)_n$ or

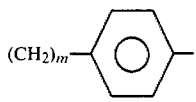

m is an integer from 0 to 10; and n is an integer from 1 to 10, and, D is an aliphatic backbone containing polymerized units of the vinylidene monomer. Excellent results were obtained when m was 0 and n was 2.

The hydroxyl containing disulfide has the formula

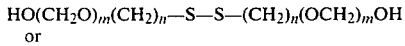

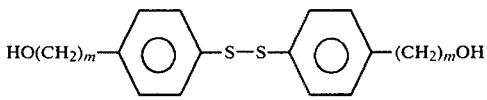

wherein, m and n have the same connotation as hereinabove.

The preparation of dithiodialkylene glycols is described in U.S. Pat. Nos. 2,746,994 and 2,754,333; and of polythiodiglycols in U.S. Pat. No. 3,778,478 ("the '478 patent"). In the process of the '478 patent, when diethanol disulfide (hereafter referred to as "DEDS" for brevity) is desired, it is formed in a first reaction by adding the stoichiometrically required amount of sulfur, to ethylene oxide dissolved in a solvent through which $H_2S$ is bubbled. DEDS is also named 2,2'-dithiodiethanol, or bis(2-hydroxyethyl) disulfide, or 2,2'-dihydroxydiethyl disulfide, or diethanol disulfide, or dithiodiglycol, or diethylene glycol disulfide, and less correctly, 2-hydroxyethyl disulfide. Though the DEDS is predominantly formed as expected, there is also formed an unpredictable amount of diethanol trisulfide (hereafter referred to as "DETS" for brevity). Thus the mixture has an unpredictable ratio of the di- and trisulfides.

Thereafter, an analogous second reaction is repeated with the stoichiometric amount of sulfur required to form the DETS. Though the trisulfide is predominantly formed as expected, there is also formed an unpredictable amount of di-and tetrasulfides. The content of the di- and tetrasulfides in the second reaction is determined; if the tetrasulfide content is not high enough to be a problem, the reaction products of the first and second reactions are mixed in the proportions required to yield a predetermined ratio of di- and tri-sulfides. Though the foregoing procedure does yield any preselected ratio of di- and tri-sulfides, it is time-consuming and relatively more costly than the two-step process of my invention which process requires no analysis of reaction products, because the process yields only a mixture of di- and tri-sulfides in the preselected ratio.

Other preparations for polysulfides are disclosed in a chapter on "Organic Sulfur Compounds", in ORGANIC CHEMISTRY, Vol. I, 2d edition by Gilman, J. Wiley & Sons, New York; and in an article titled "$\beta\beta'$-dichlorodiethyl disulfide" in J. Chem. Soc., 119, 418 (1921), by Bennet, G. M.

During the investigation of sulphur vesicants, reported in an article titled "New Organic Vesicants. Part IV. 1:2-Di-(2-chloroethylthio)ethane and its Analogues" by Gasson, E. J. Williams, A. H. and Woodward F. N., J. Chem. Soc. (London), 44 (1948), 2-hydroxyethanethiol was oxidized by the careful addition of 30.5% w/v hydrogen peroxide, the temperature being kept below 50°. After removal of the water under low pressure, a thick colorless syrup remained which could not be induced to crystallise, but could be distilled in small batches, if done quickly. The pure dihydroxy-disulfide (DEDS) was obtained as an intermediate which was then converted to the chloro-compound by means of thionyl chloride.

SUMMARY OF THE INVENTION

A simple and convenient two-step process has been discovered for the preparation of a mixture of hydroxyl-containing di- and trisulfides, starting with a mercapto-lower alkanol. The particular mercapto-lower alkanols which can be used in this process are 2-mercaptoethanol, and, 3-mercaptopropanol, because they can be oxidized with hydrogen peroxide to yield the corresponding dialkanol disulfides, substantially to the exclusion of deleterious byproducts, if a stoichiometric amount of $H_2O_2$ is used, and, if the pH and temperature ranges of an exothermic reaction yielding the disulfide is carefully controlled. To carry out the process in two steps in a single reaction vessel, the exothermic reaction must proceed in the vessel in a reaction mixture which is a relatively dilute aqueous solution the pH of which is maintained in the range from 7 to 9, and the temperature maintained below 20° C. but above the freezing point of the reaction mixture. Thereafter, a predetermined amount of sulfur is added to the reaction mixture in the vessel, and the dialkanol trisulfide is formed by regulating the rate at which the reaction mixture is heated. The mixture of di- and trisulfides formed is free of byproducts deleterious to the formation of hydroxyl-terminated liquid polymers having an aliphatic polymeric backbone and sulfide linkages.

A chain terminator which is a mixture of hydroxyl-containing disulfide and trisulfide derived in a preselected ratio from a mercapto-lower alkanol, yields excellent HTPS polymers defined by the formula

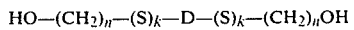

wherein, D is an aliphatic backbone containing polymerized units of a vinylidene monomer, n is either 1 or 2, and k is either 1 or 2. These HTPS polymers are obtained with better control of molecular weight, and some of the polymers not only have more desirable physical and chemical properties, but also may be produced more economically, using less polysulfide chain terminator than in the '766 process.

DETAILED DESCRIPTION OF THE INVENTION

In preferred embodiments of this invention, a mixture of dialkanol disulfide and trisulfide is produced in two steps, from a mercapto-lower alkanol. By "dialkanol" I refer specifically to the dialkanols of lower alkanols ethanol and propanol, and by a "mercapto-lower alkanol" I refer specifically to 2-mercaptoethanol and 3-mercaptopropanol. The process will be described hereinafter with respect to starting with 2-mercaptoethanol, it being understood that 3-mercaptopropanol may be used in an analogous manner. The preselected ratio of disulfide and trisulfide desired in the mixture will vary according to the desired polymeric molecular weight of the HTPS polymer, but typically the amount of the mixture is from about 1 to about 20 percent by weight ("wt %") of the HTPS polymer formed. The dialkanol trisulfide typically constitutes from about 1 to about 25 wt % of the disulfide-trisulfide mixture, and more preferably from about 2 to about 10 wt %. Excellent results in the control of the molecular weight of the HTPS polymer formed, and therefore of its physical and chemical properties, are obtained using a mixture of about 95 wt % DEDS and 5 wt % DETS.

The process of this invention is conveniently carried out in a single reaction vessel, such as a jacketed kettle, in a first step in which the 2-mercaptoethanol is reacted with a stoichiometric amount of hydrogen peroxide in a reaction mixture which is a relatively dilute aqueous solution, while the pH and temperature are maintained in specified narrow ranges to prevent the formation of deleterious byproducts.

The relatively dilute reaction mixture of the first step initially includes 2-mercaptoethanol and water in the ratio of from about 3:1, to about 1:3 by wt. respectively. When a ratio of about 3:1 is used, the refrigeration demand for cooling the kettle may be quite high, particularly if the 2-mercaptoethanol and water are each at about room temperature (20° C.), and not precooled, when they are mixed. In more dilute reaction mixtures, where there is more water than 2-mercaptoethanol by wt, it is easier to control the exothermic reaction which occurs upon addition of hydrogen peroxide. A dilution where the ratio of 2-mercaptoethanol to water is greater than 1:3 does not adversely affect the course of the reaction, but the presence of the additional water may be a burden if it is to be removed later. It is most preferred to start with a ratio in the range from about 2:1 to about 1:1 parts by wt of 2-mercaptoethanol to water to minimize additional cooling requirements and the cost of water removal after the mixture of disulfide and trisulfide is formed.

A stoichiometric amount of hydrogen peroxide is added, preferably as an aqueous solution such as is readily available commercially in the range from about 30 to about 40% w/v $H_2O_2$. The reaction proceeds quickly so the rate at which the $H_2O_2$ is added must be such as not to exceed the temperature limitation of 20° C. It will be evident that the reaction mixture will be diluted as aqueous $H_2O_2$ is added, and this dilution facilitates control of the reaction. But it is essential that an excess of $H_2O_2$ be avoided or further oxidation of the dihydroxy-disulfide formed takes place unpredictably. Therefore only a stoichiometric amount of $H_2O_2$ is added, and when this is done, it is not necessary to check whether or not all the 2-mercaptoethanol has been converted to the dihydroxy-disulfide by chromatographic analysis of the reaction mixture.

The formation of byproducts deleterious to the subsequent direct use of the products of this invention, upon concentration by water removal but without purification, as a chain terminator for HTPS polymers, is further inhibited if the pH of the reaction mixture is maintained between 7 and 9. The pH is controlled by adding any alkaline water-soluble material, and only a very little, less than 0.1% by wt based on the 2-mercaptoethanol, will usually suffice. Preferred alkaline materials to control the pH are the alkali metal hydroxides, sodium hydroxide and potassium hydroxide being most preferred.

It has also been found that the formation of deleterious byproducts is still further inhibited by maintaining the temperature of the contents of the kettle in the range below 20° C. but above the freezing point of the reaction mixture. It is most preferred to maintain the temperature in the range from about 5° to about 15° C.

In the second step of the process, a stoichiometric amount of sulfur, sufficient to form from about 2 to about 10 wt % of the 2-hydroxyethyl trisulfide, is added, and the contents controlledly heated so that the temperature increases at the rate of about 1° C. per minute, preferably from about 0.25 to about 0.5° C./min, but does not exceed 100° C. while the reaction proceeds. It may be desirable to allow the contents of the kettle to cook for a short period of time during which a chromatographic analysis may be made to confirm the presence of the desired amount of trisulfide. The contents of the kettle are then removed and subjected to evaporation in a thin-film evaporator under reduced pressure, to remove the water if a water-free mixture of di- and trisulfides is desired. Alternatively, the water may be removed by vacuum distillation, or any other method which does not adversely affect the polysulfides in the mixture. A water-free mixture of the polysulfides is preferred when it is to be used for a reaction with a vinylidene monomer to produce an HTPS polymer of controlled molecular weight.

The aliphatic backbone contains polymerized units of at least one terminal $CH_2=C<$ group. The vinylidene monomer is selected from the group consisting of (a) monoolefins containing 2 to 14 carbon atoms, more preferably 2 to 8 carbon atoms, such as ethylene, propylene, isobutylene, 1-butene, 1-pentene, 1-hexene, 1-dodecene and the like; (b) dienes containing 4 to 10 carbon atoms, more preferably 4 to 8 carbon atoms, such as butadiene, isoprene, 2-isopropyl-1,3-butadiene, and the like; (c) vinyl and allyl esters of carboxylic acids containing 2 to 8 carbon atoms such as vinyl acetate, vinyl propionate, allyl acetate, and the like; (d) vinyl and allyl ethers of alkyl radicals containing 1 to 8 carbon atoms such as vinyl methyl ether, allyl methyl ether, and the like; and (e) acrylic acids and acrylates having the formula

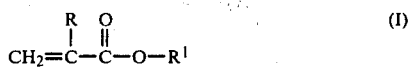

$$\begin{array}{c} R \quad O \\ | \quad \| \\ CH_2=C-C-O-R^1 \end{array} \quad (I)$$

wherein R is hydrogen or an alkyl radical containing 1 to 3 carbon atoms, and $R^1$ is hydrogen or an alkyl radical containing 1 to 18 carbon atoms, more preferably 1 to 8 carbon atoms, or an alkoxyalkyl, alkylthioalkyl, or cyanoalkyl radical containing 2 to 12 carbon atoms, more preferably 2 to 8 carbon atoms. Even more preferably $R^1$ is hydrogen or an alkyl radical containing 1 to 8 carbon atoms. Examples of suitable acrylates include ethyl acrylate, butyl acrylate, hexyl acrylate, 2-ethylhexyl acrylate, dodecyl acrylate, octadecyl acrylate, methoxyethyl acrylate, butoxyethyl acrylate, hexylthioethyl acrylate, β-cyanoethyl acrylate, cyanooctyl acrylate, methyl methacrylate, ethyl methacrylate, octyl methacrylate and the like. Often two or more types of these polymerized monomeric units are contained in the polymeric backbone.

More preferred among the foregoing liquid polymers contain polymerized units of at least one vinylidene monomer having at least one terminal $CH_2=C<$ group and among (a) through (e) hereinabove, are selected from the group consisting of (a) monoolefins containing 2 to 8 carbon atoms; (b) dienes containing 4 to 8 carbon atoms; and (e) acrylic acids and acrylates having the formula (I) hereinabove wherein $R^1$ is hydrogen or an alkyl radical containing 1 to 8 carbon atoms. Excellent results were obtained with alkyl acrylates wherein the alkyl group contained 1 to 8 carbon atoms, including a butyl acrylate and ethyl acrylate.

The vinylidene monomers described above may be polymerized readily with from 0% to about 40% by weight, more preferably from 0% to about 25% by weight, of at least one copolymerizable ethylenic monomer. Suitable comonomers include those selected from the group consisting of (f) vinyl aromatics having the formula

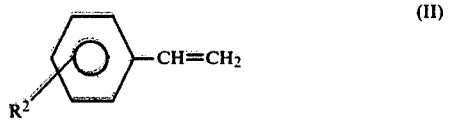

wherein $R^2$ is hydrogen, halogen, an alkyl or hydroxyalkyl radical containing 1 to 4 carbon atoms, such as styrene, α-methyl styrene, chlorostyrene, vinyl toluene, and the like; (g) vinyl nitriles having the formula $$\begin{array}{c} R^3 \\ | \\ CH_2=C-C\equiv N \end{array} \quad (III)$$

wherein $R^3$ is hydrogen or an alkyl radical containing 1 to 3 carbon atoms, such as acrylonitrile, methacrylonitrile and the like; (h) divinyls and diacrylates such as divinyl benzene, divinyl ether, diethylene glycol diacrylate, and the like; (i) amides of α,β-olefinically unsaturated carboxylic acids containing 2 to 8 carbon atoms such as acrylamide and the like; (j) hydroxyl-containing vinylidene monomers for the purpose of including some random hydroxyl functionality, for example allyl alcohol, vinyl benzyl alcohol, and hydroxylcontaining esters of acrylic acid such as 2-hydroxyethyl acrylate and the like; and (k) other vinylidene monomers such as bis(β-chloroethyl)-vinyl phosphonate, N-vinyl-2-pyrrolidone, diacetone acrylamide, and the like. Liquid polymer compositions comprising polymerized units of a major amount of at least one vinylidene monomer listed in (a) to (e) hereinabove, with a minor amount of at least one comonomer listed in (f) to (k) are within the scope of this invention.

More preferred among the above comonomers may be selected from the groups designated (f), (g), (j) and (k) hereinabove. Excellent results were obtained using acrylonitrile, 2-hydroxyethyl acrylate, N-vinyl-2-pyrrolidone and diacetone acrylamide.

Examples of useful polymeric backbones in the hydroxylated liquid alkyl acrylate polymers include poly(n-butyl acrylate/N-vinyl-2-pyrrolidone/butadiene/acrylic acid), wherein the acrylic acid moiety is hydroxylated after polymerization using ethylene oxide or the like to provide random hydroxyl group(s) in a backbone unit equivalent to 2-hydroxyethyl acrylate. Also suitable are poly(n-butyl acrylate/N-vinyl-2-pyrrolidone/2-hydroxyethyl acrylate), poly(nbutyl acrylate/ethyl acrylate/N-vinyl-2-pyrrolidine/2-hydroxyethyl acrylate, poly(n-butyl acrylate/butadiene/N-vinyl-2-pyrrolidine/2-hydroxyethyl acrylate), and poly(n-butyl acrylate/ethyl acrylate/acrylonitrile/2-hydroxyethyl acrylate). In the latter four backbones, random hydroxylation is provided using 2-hydroxyethyl acrylate. Of course, each polymer backbone has terminal hydroxyl functionality provided by the hydroxyl-containing disulfide and hydroxyl-containing trisulfide as described heretofore.

The following illustrative example describes the preparation of a mixture of DEDS and DETS in a typical pilot plant run.

EXAMPLE 17.6 lb of cool water at about 12° C. is run into a jacketed glass-lined kettle appropriately piped to permit its contents to be heated or cooled as desired, by circulating a heat transfer fluid in the kettle's jacket. 29.3 lb of 2-mercaptoethanol are then added to the kettle with stirring, with cooling, so that the contents of the kettle are maintained at about 10° C. Then 18.2 lb of 35% w/v $H_2O_2$ are slowly dripped into the kettle, while stirring, and sufficient NaOH is added to keep the pH at about 8. A total of 21.5 gm of NaOH is usually sufficient. If the addition of $H_2O_2$ is sufficiently slow, the contents of the kettle can be kept below 20° C. by circulating water from the mains. If the addition rate of $H_2O_2$ is increased, refrigerated water or other liquid may be necessary. Stirring of the contents of the kettle is continued for about 1 hour after all the $H_2O_2$ has been added, and the contents are then allowed to warm to room temperature. At the end of this first step of the process, the reaction product is substantially pure DEDS which crystallizes upon cooling.

In the second step of the process, 127 gm (0.28 lb) of pure sulfur is added to the aqueous DEDS in the kettle, while stirring. Stirring is continued while hot water is introduced into the jacket, gradually displacing the room temperature water, and increasing the temperature of the contents of the kettle slowly, at less than about 1°/min, and preferably at about 0.5°/min. It may be necessary to use steam for heat transfer at a heating rate approaching 1°/min. Higher rates are found to produce tetrasulfides and other difficult to identify byproducts which are deleterious to the subsequent formation of HTPS polymers having controlled molecular weight. The heating of the contents of the kettle is continued until they reach but do not exceed 100° C., at which temperature they are permitted to 'cook' for about an hour. A temperature in excess of 100° C. causes scission of sulfide links and a random recombination of various moieties in an unpredictable manner to yield undesirable byproducts. At the end of this second step of the process, essentially all the added sulfur in this second step is taken up in the formation of DETS.

The contents of the kettle are vacuum distilled, after which a pure liquid mixture of DEDS and DETS is obtained in about 97% yield. The ratio of DEDS to DETS is found to be about 95:5. This mixture is used directly in the formation of HTPS polymers named hereinabove.

I claim:

1. A two-step process for the preparation of a mixture of hydroxyl-containing disulfide and trisulfide starting with a mercapto-lower alkanol, comprising, in a first step, (a) adding a stoichiometric amount of $H_2O_2$ to an aqueous mixture of said mercapto-lower alkanol in a reaction vessel, (b) maintaining said vessel's contents at a pH in the range from 7 to 9, (c) maintaining said contents at a temperature in the range from above their freezing point but below 20° C., and (d) forming an essentially pure dihydroxy-disulfide; and, in a second step, (e) adding a predetermined amount of sulfur to the contents of said vessel sufficient to form a dihydroxy-trisulfide in a predetermined ratio from about 1 to about 25 percent by weight of disulfide-trisulfide mixture, (f) heating the contents at a rate less than 1°/minute to a maximum temperature of 100° C., and, (g) recovering a mixture of dihydroxy-disulfide and dihydroxy-trisulfide in said predetermined ratio.

2. The process of claim 1 wherein said mercapto-lower alkanol is selected from 2-mercaptoethanol and 2-mercaptopropanol.

3. The process of claim 2 wherein maintaining said pH range includes adding less than 0.1 percent by weight based on said mercapto-lower alkanol, of an alkali metal hydroxide.

4. The process of claim 3 wherein said essentially pure dihydroxy-disulfide is crystallizable from aqueous solution.

5. The process of claim 3 wherein said dihydroxy-trisulfide constitutes from about 2 to about 10 percent by weight of said disulfide-trisulfide mixture.

6. The process of claim 5 wherein, in said second step, heating said contents is effected at a rate in the range from about 0.25° to about 0.5° C. per minute.

* * * * *